(12) United States Patent
Ishiwari et al.

(10) Patent No.: US 6,609,415 B2
(45) Date of Patent: Aug. 26, 2003

(54) METHOD OF EVALUATING ADSORPTION OF CONTAMINANT ON SOLID SURFACE

(75) Inventors: Syuichi Ishiwari, Chiyoda-ku (JP); Haruo Kato, Ome (JP)

(73) Assignee: Hitachi Plant Engineering & Construction Co., Ltd., Tokyo (JP)

( * ) Notice: Subject to any disclaimer, the term of this patent is extended or adjusted under 35 U.S.C. 154(b) by 89 days.

(21) Appl. No.: 09/801,685

(22) Filed: Mar. 9, 2001

(65) Prior Publication Data

US 2001/0025524 A1 Oct. 4, 2001

(30) Foreign Application Priority Data

Mar. 21, 2000 (JP) .......................... 2000-078650

(51) Int. Cl.$^7$ .................. B23Q 17/09; G01N 1/00; G01N 1/07; G01N 19/02; G01N 27/62
(52) U.S. Cl. .................. 73/104; 73/31.03; 73/865.8; 73/866
(58) Field of Search ................. 73/104, 31.03, 73/865, 865.6, 865.8, 866; 206/710

(56) References Cited

U.S. PATENT DOCUMENTS 6,120,584 A * 9/2000 Sakata et al. ................. 96/135
6,125,689 A * 10/2000 Graves et al. ............. 73/23.37

FOREIGN PATENT DOCUMENTS

| JP | 9-171002 | * | 6/1997 |
| JP | 2000-28596 | * | 1/2000 |

OTHER PUBLICATIONS

English language translation of JP 9–171002 (Sakata et al.).*

* cited by examiner

Primary Examiner—Daniel S. Larkin
(74) Attorney, Agent, or Firm—Oliff & Berridge, PLC

(57) ABSTRACT

A test piece made of a material equal to the material of the workpiece is formed in a size that permits the test piece to be housed in an adsorption tube container mounted to a mass analyzing apparatus of a gas chromatograph. The test piece is left to stand for a predetermined time in a measuring site of the atmosphere within a cleansing chamber and, then, recovered. The recovered test piece is introduced into a mass analyzing apparatus of a gas chromatograph (GC-MS apparatus) for measurement of the material of the contaminant and the mass of the contaminant, thereby evaluating the degree of contamination of the measured point.

4 Claims, 7 Drawing Sheets adsorbed organic impurities on Si surface by Si single plate method organic impurities in atmosphere by Tenax adsorption tube

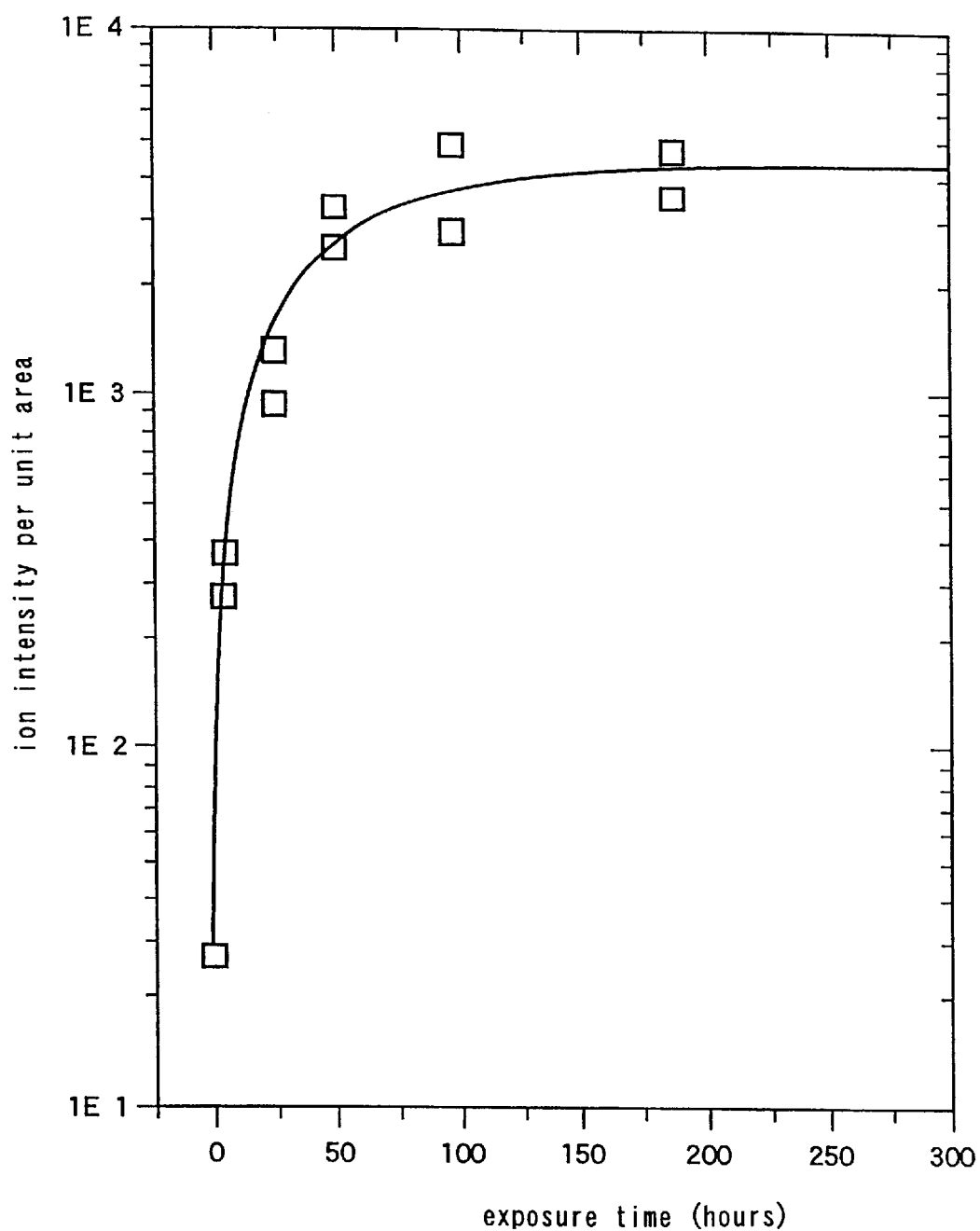

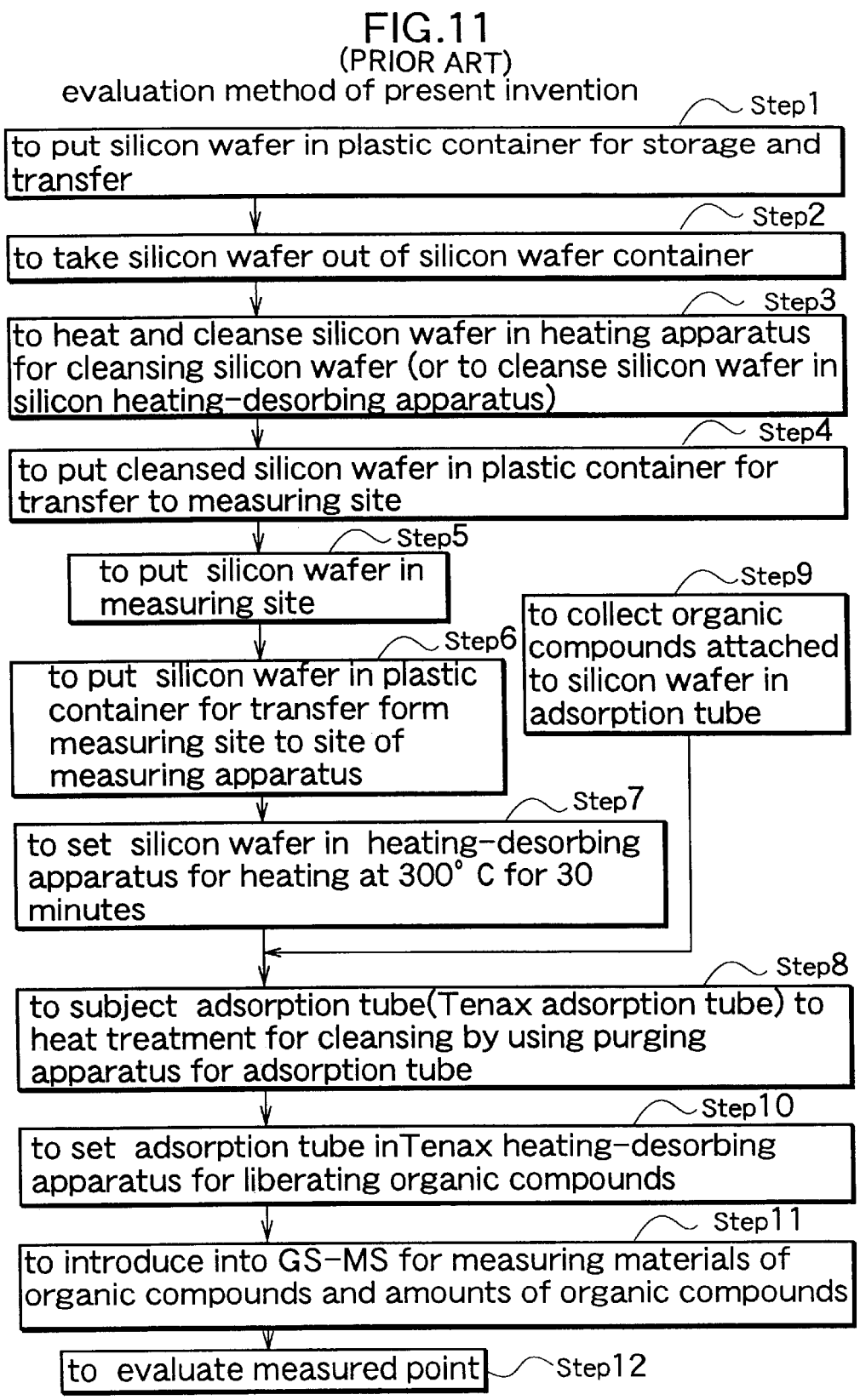

METHOD OF EVALUATING ADSORPTION OF CONTAMINANT ON SOLID SURFACE

BACKGROUND OF THE INVENTION

1. Field of the Invention

The present invention relates to a method of evaluating the adsorption of contaminants on a solid surface, particularly, to a method adapted for measuring the amount of adsorption of contaminants floating in a cleansing room, such as a clean room, on a workpiece, such as a silicon wafer, and for evaluating the cleanliness within the cleansing room and the contamination of the workpiece itself or on the cut solid surface.

2. Description of the Related Art

In accordance with progress in the degree of integration of the semiconductor device, the semiconductor device has been miniaturized and a multi-layered structure has come to be widely employed. In this connection, the manufacturing process of the semiconductor device has come to be affected by various impurities. It is known to the art that the manufacturing process of the semiconductor device is more or less affected by traces of, i.e., about picograms ($10^{-12}$ g) of, all the atoms and molecules except silicon. Particularly, many kinds of organic compounds represented by carbon compounds are used in the manufacturing process of the semiconductor device. For example, a photoresist material, which is a typical organic compound, is used twenty times or more in the manufacturing process of the semiconductor device. Also, many materials generating organic compounds are used in a cleansing room, such as a clean room. For example, a plastic material is used in the duct, piping, wall material, and floor material. What should be noted is that a large amount of an organic compound, such as dibutyl phthalic acid (DBP) or dioctyl phthalic acid (DOP), is contained as a plasticizer in the plastic material. Such an organic compound contained in the plasticizer, which provides a contaminant, is evaporated from the duct, piping, wall material, floor material, etc. even under a low pressure and room temperature so as to float within the clean room. Such a floating contaminant is adsorbed on the workpiece, such as a silicon wafer, so as to contaminate the workpiece. Other contaminants, such as silicon, quartz, glass, and a metal material, also float within the clean room.

The methods for measuring the contamination includes, for example, a method for evaluating the contaminant, such as an organic compound, which is adsorbed on the wafer surface. In this method, the wafer itself is left to stand within an atmosphere so as to be measured by a wafer heating desorption type gas chromatograph for the mass analysis.

The conventional evaluation method referred to above will now be described with reference to FIG. 11. As shown in the drawing, a silicon wafer transferred and stored in a plastic container is taken out of the plastic container (steps 1 and 2), and is heated in a heating device for cleansing the silicon wafer so as to remove the contaminant from the silicon wafer (step 3), thereby cleansing the silicon wafer. Alternatively, it is possible to cleanse the silicon wafer by using a heating-desorbing device of a silicon wafer. In this case, however, the number of analyses and measurements performed in a unit time is reduced by half. The cleansed silicon wafer is housed again in the plastic container and is transferred to a measuring site within a chamber, such as a clean room (step 4). The silicon wafer is taken out of the plastic container at the measuring site and is left to stand for a predetermined time (one to two hundred hours) in the measuring site (step 5). The silicon wafer having an organic compound adsorbed thereon is housed again in the plastic container so as to be transferred to the point of a measuring device. Then, the silicon wafer is taken out of the plastic container and, is set in a heating-desorbing device for a silicon wafer so as to be heated at 300° C. for thirty minutes (steps 6 and 7).

The organic compound generated from the heated silicon wafer is caught by an absorption tube (trade name of Tenax Absorption Tube) containing an activated carbon (step 8). Then, the adsorption tube is subjected to a heat treatment at 280° C. for three hours by using an adsorption tube purging apparatus (trade name of Tenax adsorption tube purging apparatus), followed by washing the adsorption tube (step 9). Since the adsorption tube set in the heating-desorbing apparatus for the silicon wafer is heated, the organic compound is liberated (step 10). Further, the adsorption tube is mounted to a gas chromatograph for the mass analysis for the measurement of the material and mass of the liberated organic compound (step 11). It is evaluated whether or not the measured point is contaminated with the organic compound based on the result of the measurement (step 12).

Also known is a method in which a silicon powder is put in an adsorption tube and the air is sucked from, for example, a clean room into the adsorption tube for performing a desired measurement.

However, in the conventional method described above, in which a silicon wafer is used and the organic compound adsorbed on the wafer surface is evaluated, it is necessary to use first a heating apparatus for cleansing the silicon wafer and a heating-desorbing apparatus for the silicon wafer for liberating the organic compound adsorbed on the silicon wafer. The heating apparatus for cleansing the silicon wafer and the heating-desorbing apparatus for the silicon wafer give rise to problems. Specifically, these apparatuses are bulky, require a large mounting area, and are costly. Also, required is a Tenax adsorption tube.

It should also be noted that the cleansed silicon wafer and the silicon wafer having a contaminant, such as an organic compound adsorbed thereon, are housed in the same plastic container for the transfer and storage. As a result, the contaminant, such as an organic compound, is evaporated from the plastic container and is adsorbed on the silicon wafer so as to lower the measuring accuracy. Further, since the silicon wafer whose contaminant has been measured is stored in the plastic container for the transfer and storage, making it impossible to store the silicon wafer for a long time. It follows that the measuring site is limited to locations in the vicinity of the heating apparatus for cleansing the silicon wafer and the heating-desorbing apparatus for the silicon wafer. As a result, it is necessary to newly install the bulky and costly heating apparatus for cleansing the silicon wafer and heating-desorbing apparatus for the silicon wafer in the case where the measuring site is located far away, e.g., where the measuring site is located overseas. An additional problem to be noted is that the use of the heating apparatus for cleansing the silicon wafer and the heating-desorbing apparatus for the silicon wafer leads to an increase in the number of measuring steps, making it difficult to carry out the required evaluation promptly.

Also, the evaluating concentration of the contaminant, e.g., dioctyl phthalic acid (DOP), adsorbed on the silicon wafer is 0.2 nanogram (ng)/cm$^2$. On the other hand, the gas chromatograph mass analyzing apparatus for detecting the contaminant has a high sensitivity and is capable of detecting DOP to an absolute concentration of 0.1 ng. However, in the case of using a silicon wafer, the silicon wafer has a surface area of 314 cm² on one surface because the silicon wafer has a diameter of 200 mm. Therefore, the concentration corresponding to the detectable sensitivity noted above is 0.1 ng/314 cm²=0.00032 ng/cm². Naturally, the sensitivity is excessively high, compared with the required sensitivity of 0.2 ng/cm².

Also known is a method in which a silicon powder or pellets are put in an adsorption tube, and air within, for example, a clean room is sucked into the adsorption tube for carrying out the required measurement. In this method, however, the silicon powder or pellets put in the adsorption tube are caused to overlap with each other, with the result that the adsorption of the organic material on the silicon wafer is deviated. Clearly, this method is not adapted for the evaluation of the organic material adsorbed on the silicon wafer.

SUMMARY OF THE INVENTION

The present invention, which has been achieved in an effort to overcome the above-noted problems inherent in the prior art, relates to a method of evaluating the adsorption of contaminants on a solid surface, and is intended to provide a method of evaluating the adsorption of contaminants on a solid surface, which permits accurate measurement and evaluation by preparing, particularly, a test piece having a small surface area so as to simplify the handling of the pretreatment, evaluation, transfer and storage, and using the wafer itself while making it unnecessary to use bulky apparatuses required in the prior art.

According to the present invention, which is intended to achieve the above-noted object, there is provided a method of evaluating the adsorption of contaminants on a solid surface, comprising the steps of preparing a test piece of a material equal to the material of a workpiece, said test piece being sized to permit the test piece to be housed in an adsorption tube container that is mounted to a mass analyzing apparatus; leaving said test piece to stand in a measuring site under a test atmosphere for a predetermined time, followed by recovering the test piece and subsequently housing the recovered test piece in said adsorption tube container; and mounting the adsorption tube container housing said test piece to said mass analyzing apparatus so as to measure the contaminant material and the mass of the contaminant, thereby evaluating the degree of contamination of the measured point.

In the present invention, it is possible to evaluate the adsorption of a contaminant on a solid surface by using as the workpiece material silicon, quartz, glass, or a metallic material, such as stainless steel, aluminum, copper, brass, or nickel silver. It is also possible to use a silicon single plate as the test piece and to use any of silicon, quartz, or a glass material for forming the adsorption tube container housing said test piece.

In the present invention of the construction described above, a test piece of a silicon single plate is prepared by cutting away a part of a silicon wafer. After the test piece is washed, the washed test piece is housed in a small adsorption tube made of a washed quartz or glass so as to be transferred to a measuring site, such as a clean room. In this step, the washed test piece is housed in an adsorption tube container that can be mounted directly to the mass analyzing apparatus of a gas chromatograph. As a result, the present invention is free from the problem inherent in the prior art that the test piece is contaminated with contaminants, such as an organic compound. Also, since the test piece is shielded from the outer atmosphere so as to be put in a hermetically sealed state, it is possible to store the test piece for a long time. At the measuring site, the test piece is taken out of the small adsorption tube container and is left to stand at the measuring site for a predetermined time. The "predetermined time" represents the time during which the contaminant reaches a predetermined surface saturation concentration, i.e., one to two hundred hours.

After the measurement, the test piece having the contaminant adsorbed thereon is housed in the small adsorption tube referred to above and transferred to the site where the measuring apparatus is installed. The small adsorption tube container housing the transferred test piece can be mounted as it is to a mass analyzing apparatus of a gas chromatograph. The mass analyzing apparatus of the gas chromatograph measures the contaminant material and the mass of the contaminant and evaluates based on the result of the measurement whether or not the measured point is contaminated with the contaminant.

Also, since the actual process wafer is cut, it is possible to evaluate the contaminant distribution within the wafer so as to contribute to the improvement in the defect analysis and yield.

BRIEF DESCRIPTION OF THE DRAWINGS

FIG. 10 is a graph relating to a surface saturation concentration owing to adsorption on a silicon single plate according to an embodiment of the present invention; and FIG. 11 is a flow chart showing the conventional method of evaluating the adsorption of organic compounds on a solid surface.

DETAILED DESCRIPTION OF THE PREFERRED EMBODIMENT

A method of evaluating the adsorption of contaminants on a solid surface according to a preferred embodiment of the present invention will now be described with reference to the accompanying drawings.

Figure 1:
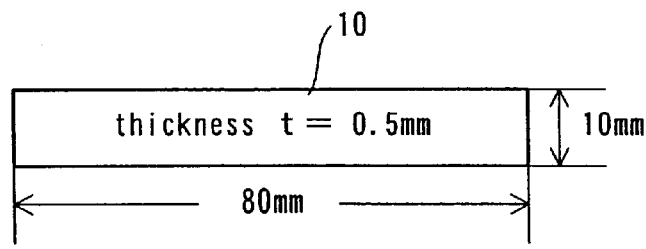
FIG. 1 is a plan view showing a silicon single plate used in a method for evaluating the adsorption of contaminants on a solid surface according to an embodiment of the present invention.

FIG. 1 is a plan view showing a silicon single plate 10 constituting an example of a test piece used in the method for evaluating the adsorption of contaminants on a solid surface according to an embodiment of the present invention. The silicon single plate 10 is prepared by cutting an ordinary silicon wafer with a diamond cutter to have a length of 80 mm, a width of 10 mm, and a thickness of 0.5 mm so as to provide a test piece used in the present invention. The size of the test piece can be determined appropriately such that the test piece can be housed in an adsorption tube container used in a mass analyzing apparatus that is to be described herein later.

Figure 2:
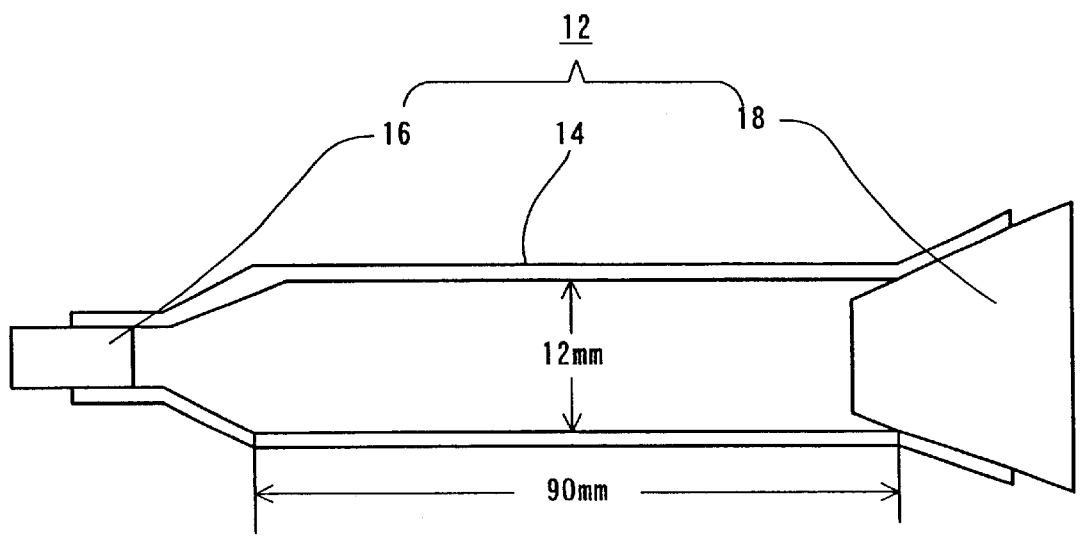
FIG. 2 is a plan view showing a quartz adsorption tube container used in a method for evaluating the adsorption of contaminants on a solid surface according to an embodiment of the present invention.
Figure 3:
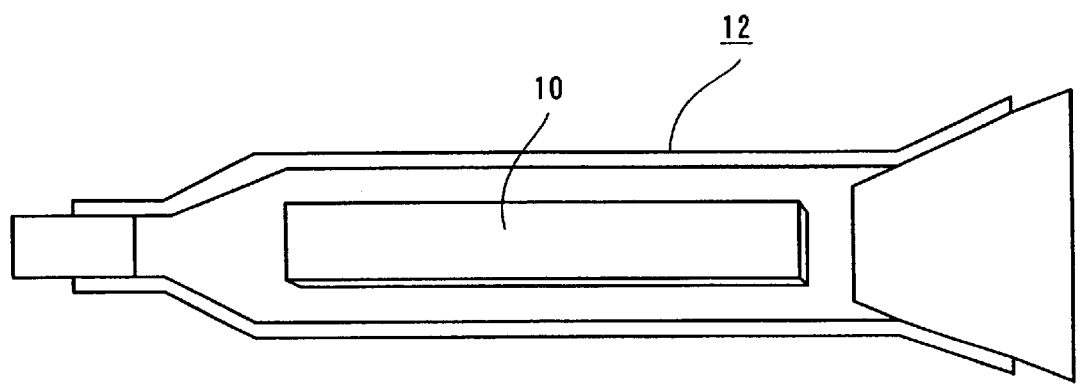
FIG. 3 is a plan view showing the state that a silicon single plate used in a method for evaluating the adsorption of contaminants on a solid surface according to an embodiment of the present invention is housed in a quartz adsorption tube container for the transfer.

FIG. 2 is a plan view showing an adsorption tube container 12 made of quartz. The quartz adsorption tube container 12 comprises a hollow cylindrical body 14, and hermetic stoppers 16, 18 inserted into both end portions of the hollow cylindrical body 14. The hollow cylindrical body 14 has an inner diameter of 12 mm and a length of 90 mm in the insertion portion. FIG. 3 is a plan view showing the state that the silicon single plate 10 is housed in the quartz adsorption tube container 12 for transfer or storage. It is possible for the adsorption tube container 12 to be formed of silicon or a glass material.

Figure 4:
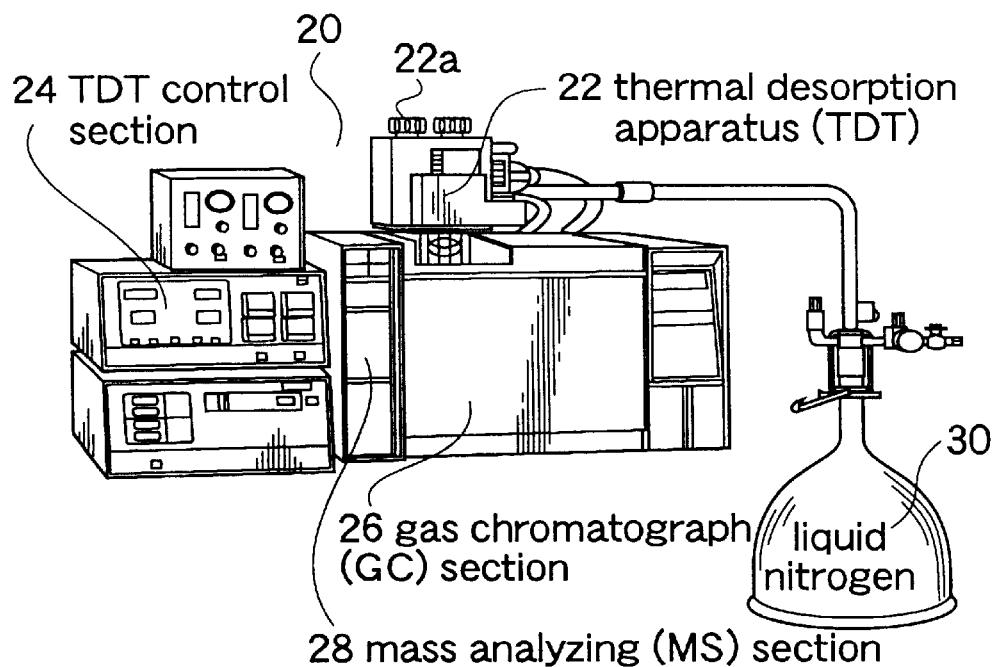
FIG. 4 shows the entire construction of a measuring apparatus used in a method for evaluating the adsorption of contaminants on a solid surface according to an embodiment of the present invention.
Figure 5:
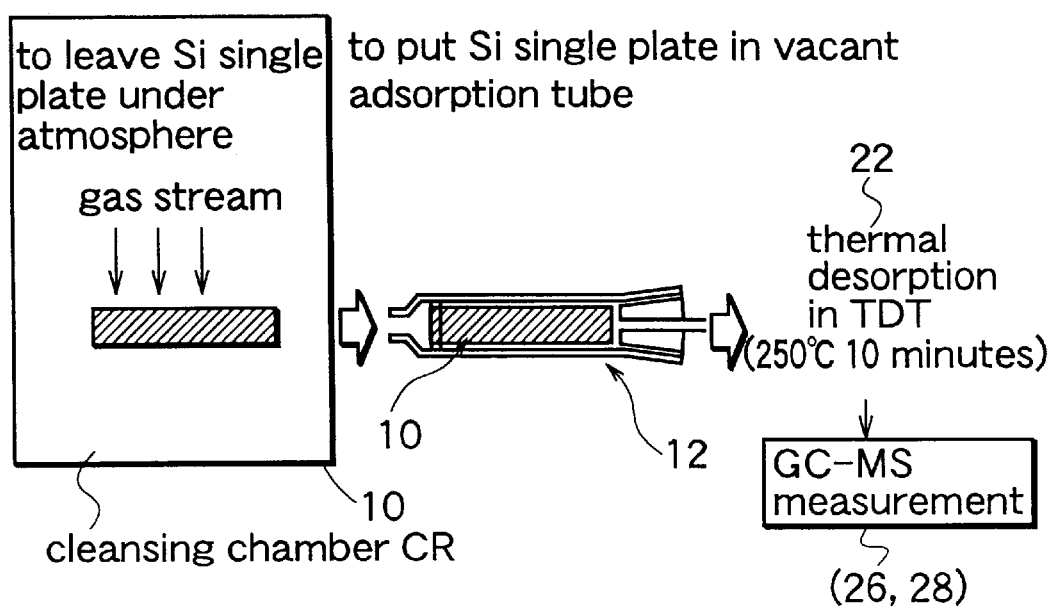
FIG. 5 is a view for explaining the method for evaluating the adsorption of contaminants on a solid surface according to an embodiment of the present invention.

FIG. 4 shows the entire construction of a measuring apparatus 20 used in the method of the present invention for evaluating the adsorption of contaminants on a solid surface. As shown in the drawing, the measuring apparatus 20 comprises a thermal desorption apparatus (TDT) 22, a thermal desorption apparatus control section 24, a gas chromatograph (GC) section 26, a mass analyzing (MS) section 28, and a liquid nitrogen section 30. The thermal desorption apparatus (TDT) is provided with a mounting section 22a through which the quartz adsorption tube container 12 is inserted in the measuring or washing step. The measuring apparatus 20 is used for the method of evaluating the adsorption of contaminants on a solid surface. As shown in FIG. 5, the silicon single plate 10 is left to stand under an atmosphere of a cleansing chamber CR, such as a clean room, in which the contaminant is measured. The silicon single plate 10 is exposed to a gaseous stream so as to have contaminants, such as dibutyl phthalic acid (DBP) or dioctyl phthalic acid (DOP), adsorbed on the surface of the silicon single plate 10. The silicon single plate 10 having the contaminant adsorbed thereon is housed in the quartz adsorption tube container 12 as shown in FIG. 3 so as to be transferred. The quartz adsorption tube container 12, which houses the silicon single plate 10, is mounted in the thermal desorption apparatus (TDT) 22. In the thermal desorption apparatus 22, the thermal desorption is carried out at, for example, 250° C. for ten minutes, and the material of the contaminant substance and the contaminant substance are measured in the gas chromatograph (GC) section 26 and the mass analyzer (MS) section 28.

As described above, the silicon single plate 10 is formed as a test piece consisting of a flat plate having a length of 80 mm and a width of 10 mm and, thus, the silicon single plate 10 has a surface area of 16 $cm^2$. As described previously, the gas chromatograph mass analyzing apparatus for detecting the contaminant has a sensitivity capable of detecting DOP to an absolute concentration of 0.1 ng. Therefore, the concentration corresponding to the detectable sensitivity is 0.1 ng/16 $cm^2$=0.006 ng/$cm^2$. It follows that the mass analyzing apparatus of the gas chromatograph has a sensitivity capable of sufficiently evaluating the required sensitivity of 0.2 ng/$cm^2$. Also, the silicon single plate 10 has a sensitivity capable of sufficiently evaluating not only dioctyl phthalic acid (DOP), but also other contaminants.

Figure 6:
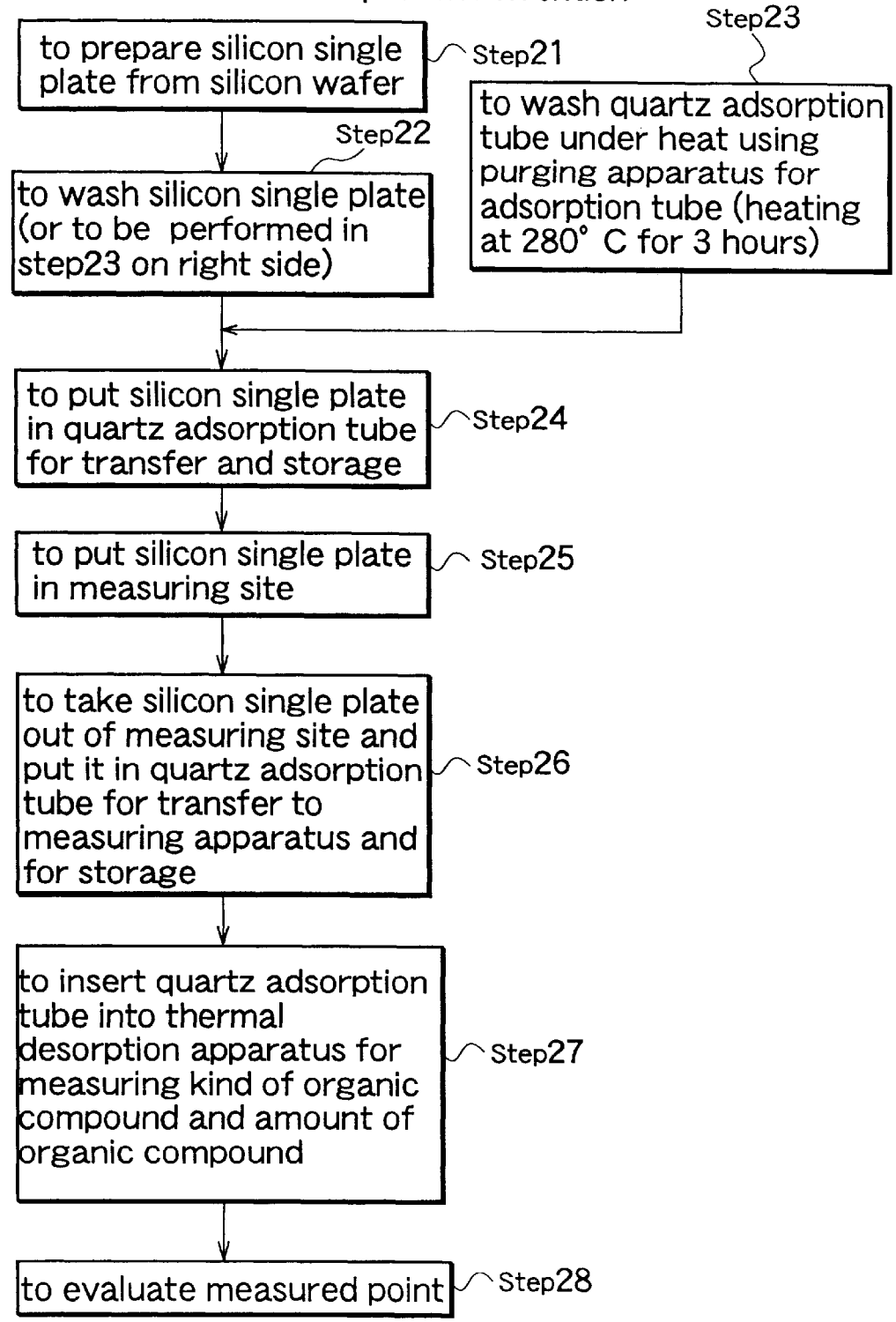
FIG. 6 is a flow chart showing the method for evaluating the adsorption of contaminants on a solid surface according to an embodiment of the present invention.

Then, the method of evaluating the adsorption of a contaminant on a solid surface according to the embodiment of the present invention will now be described in detail with reference to FIG. 6. In the first step, a test piece of the silicon single plate 10 is prepared by cutting an ordinary silicon wafer with a diamond cutter (step 21), followed by washing the silicon single plate 10. The washing is performed by using an ordinary wafer washing apparatus (step 22). Alternatively, it is possible to wash the silicon single plate 10 by using a purging apparatus for desorption, which is used for washing the quartz adsorption tube container 12 (step 23). The purging apparatus for adsorption is advantageous in that six silicon single plates 10 can be washed at a time. The washed silicon single plate 10 is housed in the quartz adsorption tube container 12 for transfer and storage (step 24). In this case, the washed silicon single plate 10 is housed in the quartz adsorption tube container 12 made of the same material. Therefore, the present invention is free from the problem inherent in the prior art that the silicon single plate 10 is contaminated with the contaminants, such as an organic compound, making it possible to store the silicon single plate 10 over a long period exceeding about two weeks. It follows that, even if the measuring site is located far away, it is possible to transfer the silicon single plate 10 to the measuring site for the required measurement. In the measuring site noted above, the silicon single plate 10 is taken out of the quartz adsorption tube container 12 and is left to stand for a predetermined time in the measuring site (step 25). The predetermined time is set to fall within a range of between one hour and two hundred hours during which the contaminant assumes a predetermined surface saturation concentration. The silicon single plate 10 having the contaminant adsorbed thereon is housed again in the quartz adsorption tube container 12 so as to be transferred to the site of the measuring apparatus 20 (step 26). In the measuring apparatus 20, the small stopper 16 on the left side of the measuring apparatus 20 in the drawing is detached, and the quartz adsorption tube container 12 of the thermal desorption apparatus (TDT) is inserted into the measuring apparatus 20. In the thermal desorption apparatus (TDT) 22, the thermal desorption is performed at, for example, 250° C. for ten minutes. Then, the material of the contaminant is analyzed in the gas chromatograph (GC) section 26, and the amount of the contaminant is measured in the mass analysis (MS) section 28 (step 27). The result of the measurement is transferred to the thermal desorption apparatus control section 24 for evaluation as to whether or not the contaminant is lower than the reference value for the evaluation, and the result of the evaluation is displayed (step 28).

Then, it was inspected whether or not the result of the measurement of the contaminant within the atmosphere of the cleansing chamber CR, which was performed by using the silicon single plate 10, was accurate.

(Inspection 1)

Figure 7:
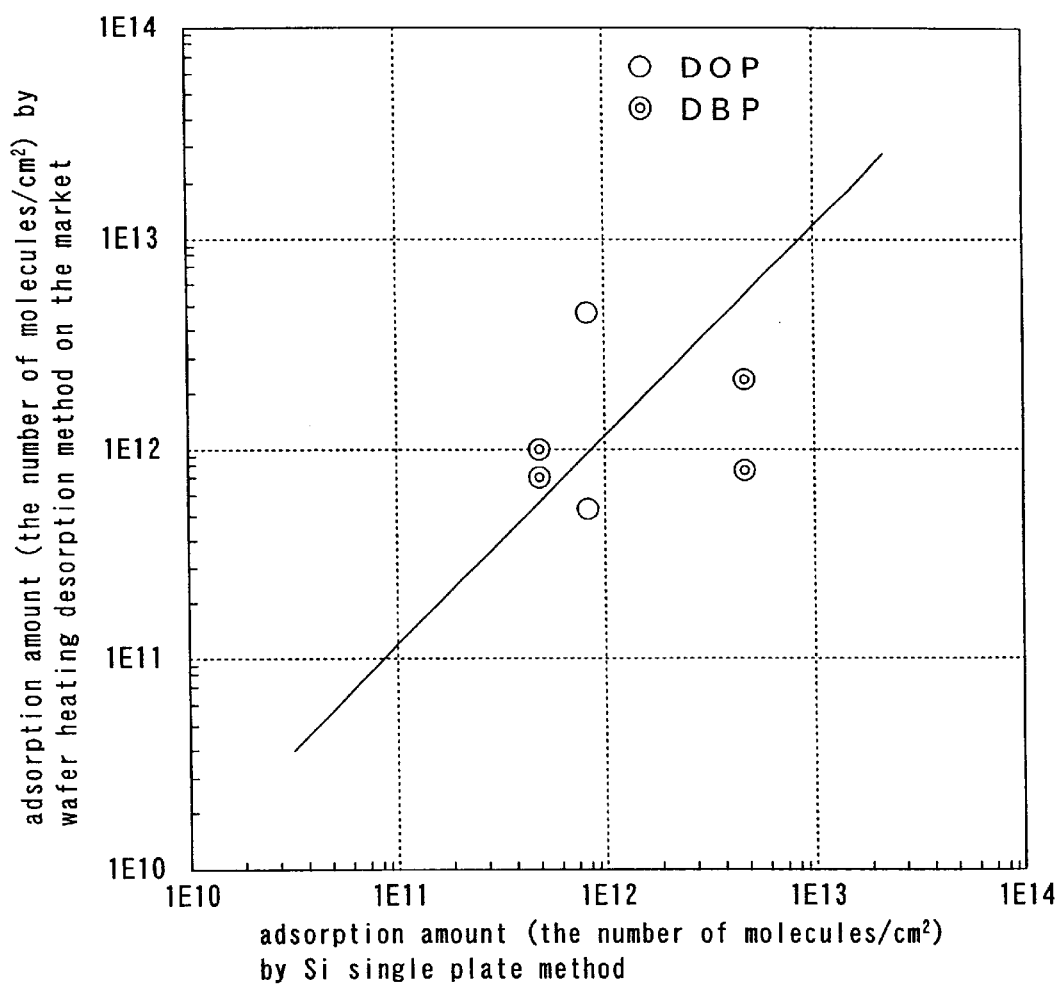
FIG. 7 is a graph comparing a measuring method using a silicon single plate according to an embodiment of the present invention with a conventional measuring method using a silicon wafer.

In the first step, the silicon single plate 10 for the present invention and a silicon wafer used in the past were allowed to stand under the atmosphere of the same cleansing chamber CR. The result in the case where the silicon single plate 10 was measured by the method shown in FIG. 6 was compared with the result in the case where the silicon wafer was measured by the method shown in FIG. 11. These results have a correlation as shown in a graph of FIG. 7. FIG. 7 supports the evaluation that the evaluation method of the present invention is appropriate. In the graph of FIG. 7, the adsorption amount (the number of molecules/$cm^2$) on the silicon single plate 10 for the present invention is plotted on the abscissa. On the other hand, the adsorption amount (the number of molecules/cm$^2$) by the conventional desorption method utilizing the heating of the silicon wafer is plotted on the ordinate. The marks "⊙" in the graph denote the measured values of dibutyl phthalic acid (DBP), with the marks "○" denoting the measured values of dioctyl phthalic acid (DOP). The correlation line is inclined by 45°, supporting that there was a correlation.

(Inspection 2)

Figure 8:
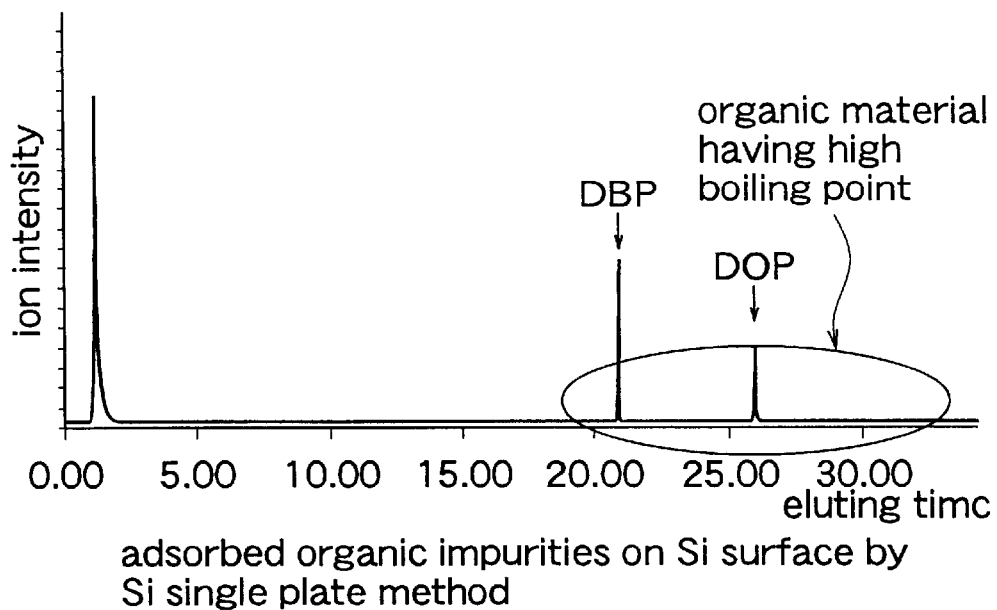
FIG. 8 is a graph showing the result of measurement of the adsorbed impurities using a silicon single plate according to an embodiment of the present invention.
Figure 9:
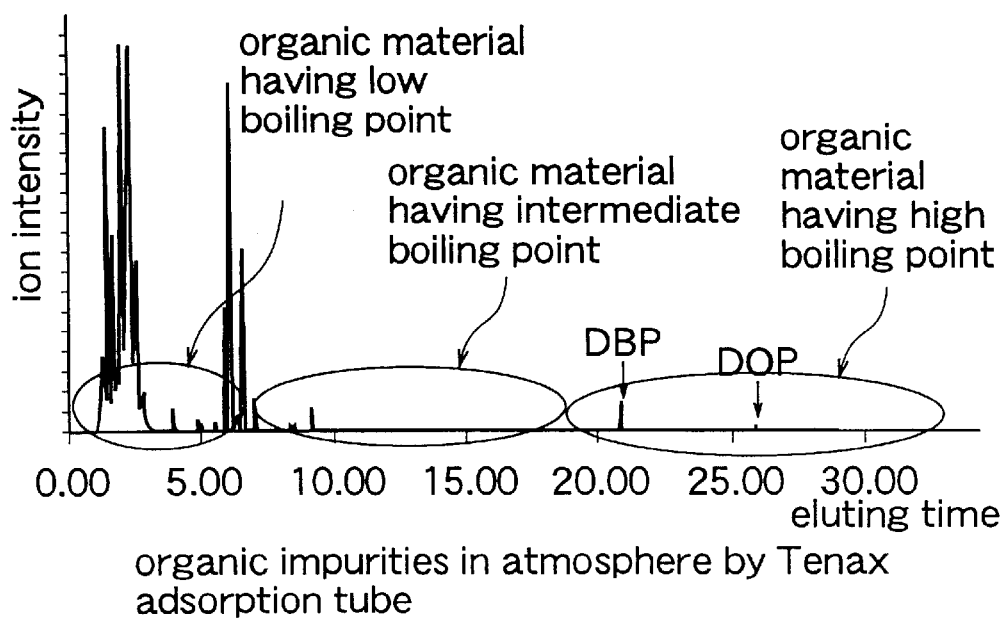
FIG. 9 is a graph showing the result of measurement of the adsorbed impurities under an atmosphere using the conventional Tenax adsorption tube.

In inspection 2, the silicon single plate 10 for the present invention was left to stand under the atmosphere of the cleansing chamber CR. Also, the air was sucked from the position where the silicon single plate 10 was left to stand into a sample tube so as to analyze the air in the atmosphere within the cleansing chamber CR. The ion intensity was measured by a GC-MC spectrum in respect of organic compounds on the basis of the silicon single plate 10 and the air in the atmosphere within the cleansing chamber CR. FIG. 9 shows that organic compounds having a low boiling point, organic compounds having an intermediate boiling point, and organic compounds having a high boiling point were analyzed from the air of the atmosphere within the cleansing chamber CR. On the other hand, FIG. 8 shows that, although organic compounds having a low boiling point and organic compounds having an intermediate boiling point are adsorbed on the silicon single plate 10, organic compounds having a high boiling point are finally substituted on the surface of the silicon single plate 10 and the organic compounds having a high boiling point are analyzed. What should be noted is that, since the organic compounds that are actually adsorbed on the surface of a silicon wafer, i.e., dibutyl phthalic acid (DBP) and dioctyl phthalic acid (DOP), can be detected, the analysis conforming with the actual situation can be performed. In conclusion, it has been confirmed that, according to the evaluation method of the present invention using the silicon single plate 10, it is possible to detect appropriately the organic compounds having a high boiling point, which are adsorbed on the silicon wafer.

(Inspection 3)

It has been clarified that, in the present invention, the concentration of the organic compound adsorbed on the silicon single plate 10 is increased to reach a certain surface saturation concentration a predetermined time later, i.e., about two hundred hours later, as apparent from a graph of FIG. 10. In the graph of FIG. 10, the exposure time during which the silicon single plate 10 was left to stand under the atmosphere is plotted on the abscissa, with the surface saturation concentration of the contaminant adsorbed on the silicon single plate 10 being plotted on the ordinate. It has also been clarified that, since the relationship between the exposure time and the surface concentration of the contaminant adsorbed on the silicon single plate 10 has been grasped, it is possible to estimate the surface saturation concentration within the atmosphere from the surface concentration of the contaminant adsorbed on the surface of the silicon single plate 10 based on the measuring time. Further, by contraries, it is possible to measure the phenomenon that DBP is expelled by DOP because of the difference in the adsorption strength between the two.

The above description covers the case where the inspection was applied to the organic compound adsorbed on silicon. However, it is also possible to evaluate the adsorption capability of the contaminant on another material by preparing a single plate having a length of 80 mm and a width of 10 mm from said another material and by allowing the single plate thus prepared to stand under an atmosphere, as far as the material does not generate an organic material upon heating at 250° C. for ten minutes under a helium gas stream. As a matter of fact, the capability of the evaluation has already been confirmed in respect of quartz, glass, and metallic materials, such as stainless steel, aluminum, copper, brass, and nickel silver. The method of the present invention can also be applied for the evaluation of the adsorption phenomenon on a solid surface, covering the case where the solid surface is treated with gases other than helium, such as oxygen, hydrogen, nitrogen, and argon. Also, there is a possibility of a small and simple sampling method using the silicon single plate 10 for evaluation of adsorption on the wafer of contaminants other than the organic compounds, such as chlorine, sulfuric acid, nitric acid, ammonia, boron, and phosphorus. It is considered desirable to utilize steam in place of heating for the desorption.

As described above, in the conventional evaluation method using a wafer heating-desorbing apparatus, it was necessary to collect the organic compounds desorbed from the wafer in a Tenax adsorption tube and to desorb the adsorbed organic compounds for the measurement from the Tenax adsorption tube in a heating-desorbing apparatus. In the method according to the embodiment of present invention, however, it is possible to introduce the organic compounds directly into the measuring apparatus, leading to the merits that the measuring accuracy can be improved, that the measurement is less obstructed, and that the adsorbed contaminants can be desorbed from the wafer in a short time. In addition, the measurement can be carried out promptly. It should also be noted that it is unnecessary in the present invention to use a wafer washing apparatus, a wafer heating-desorbing apparatus, and a Tenax adsorption tube required in the case of using a silicon wafer. It follows that the installing area of the processing facilities can be diminished and the facility cost can be reduced in the method of the present invention. What should also be noted is that, in the prior art, it was possible to use the silicon wafer only once. However, the silicon single plate used in the present invention can be used repeatedly, leading to reduction in the cost of the test piece. Further, the silicon single plate can be handled, subjected to the pretreatment, evaluated, transferred, and stored easily so as to suppress the contamination and to improve the measuring accuracy. Still further, since it is possible to use a hermetic and small transfer tool for transferring the silicon single plate, the storing time can be prolonged. In addition, it is possible to measure easily the atmosphere of a cleansing chamber located far away.

To reiterate, in the present invention, a test piece made of a material equal to the material of the workpiece is formed in a size that permits the test piece to be housed in an adsorption tube container mounted to a mass analyzing apparatus. After left to stand for a predetermined time at a measuring point under the inspecting atmosphere, the test piece is recovered and housed in the adsorption tube container. Then, the adsorption tube container housing the test piece is mounted to a mass analyzing apparatus for measuring the material of the contaminant and the mass of the contaminant. The particular construction of the present invention permits facilitating the handling of the pretreatment and the evaluation. Also, it is possible to prevent the contamination of the test piece during the transfer, storage, etc. In addition, the method of the present invention for evaluating the adsorption of the contaminant on a solid surface permits measurement and evaluation with a high accuracy while using the wafer itself and while making it unnecessary to use bulky apparatuses required in the prior art.

What is claimed is:

1. A method of evaluating the adsorption of contaminants on a solid surface, comprising the steps of:

preparing a test piece of a material equal to the material of a workpiece, said test piece being sized to permit said test piece to be housed in an adsorption tube container that is mounted to a mass analyzing apparatus;

leaving said test piece to stand in a measuring site under a test atmosphere for a predetermined time;

recovering the test piece;

disposing the recovered test piece in said adsorption tube container;

transporting the test piece housed in said adsorption tube container from the measuring site to the analyzing apparatus; and directly mounting the adsorption tube container housing said test piece to said mass analyzing apparatus so as to measure the contaminant material and the mass of the contaminant, thereby evaluating the degree of contamination of a measured point.

2. The method of evaluating the adsorption of contaminants on a solid surface according to claim 1, wherein the material of said workpiece is silicon, quartz, glass, or a glass material.

3. The method of evaluating the adsorption of contaminants on a solid surface according to claim 1, wherein said test piece consists of a silicon single plate, and the adsorption tube container housing said test piece is made of silicon, quartz, or a glass material.

4. The method of evaluating the adsorption of contaminants on a solid surface according to claim 1 wherein the material of said workpiece is silicon, quartz, glass, or a metallic material, and the adsorption tube container housing said test piece is made of silicon, quartz, or a glass material.

* * * * *